United States Patent
Perovitch et al.

(10) Patent No.: US 9,532,947 B2
(45) Date of Patent: Jan. 3, 2017

(54) FORMULATION FOR ORAL TRANSMUCOSAL ADMINISTRATION OF ANALGESIC AND/OR ANTISPASMODIC MOLECULES

(76) Inventors: Philippe Perovitch, Le Temple (FR); Marc Maury, Saint Medard En Jalles (FR)

(*) Notice: Subject to any disclaimer, the term of this patent is extended or adjusted under 35 U.S.C. 154(b) by 371 days.

(21) Appl. No.: 13/144,205

(22) PCT Filed: Jan. 12, 2010

(86) PCT No.: PCT/FR2010/050039
§ 371 (c)(1),
(2), (4) Date: Jul. 12, 2011

(87) PCT Pub. No.: WO2010/081984
PCT Pub. Date: Jul. 22, 2010

(65) Prior Publication Data
US 2011/0275626 A1    Nov. 10, 2011

(30) Foreign Application Priority Data
Jan. 13, 2009   (FR) .................... 09 50145

(51) Int. Cl.
*A61K 31/395*   (2006.01)
*A61K 31/5377*  (2006.01)
*A61K 9/00*     (2006.01)
*A61K 9/08*     (2006.01)
*A61K 47/10*    (2006.01)

(52) U.S. Cl.
CPC .......... *A61K 9/006* (2013.01); *A61K 9/08* (2013.01); *A61K 47/10* (2013.01)

(58) Field of Classification Search
CPC .......... A61K 9/006; A61K 9/08; A61K 47/10
USPC ................. 514/231, 576, 450, 395
See application file for complete search history.

(56) References Cited

U.S. PATENT DOCUMENTS

| | | | |
|---|---|---|---|
| 3,093,544 A * | 6/1963 | Lafon | A61K 31/05 514/731 |
| 6,440,453 B1 | 8/2002 | Fischer et al. | |
| 8,722,744 B2 * | 5/2014 | Perovitch et al. | 514/630 |
| 2003/0215530 A1 * | 11/2003 | Uehara et al. | 424/729 |
| 2010/0022496 A1 | 1/2010 | Perovitch et al. | |
| 2010/0041632 A1 * | 2/2010 | Zhang et al. | 514/171 |
| 2010/0093710 A1 | 4/2010 | Perovitch et al. | |
| 2010/0168238 A1 * | 7/2010 | Serrano et al. | 514/563 |

FOREIGN PATENT DOCUMENTS

| | | | |
|---|---|---|---|
| FR | 2910317 A1 | | 6/2008 |
| FR | 2918874 A1 | | 1/2009 |
| WO | WO2005/060957 | * | 7/2005 |
| WO | 2008/035020 A2 | | 3/2008 |
| WO | 2008/079295 A1 | | 7/2008 |
| WO | WO2008/087323 | * | 7/2008 |
| WO | WO2009/053742 | * | 4/2009 |

OTHER PUBLICATIONS

English translation of the Written Opinion of the International Searching Authority for PCT/FR2010/050039.
Takahashi, Koichi, et al., "Novel approach to improve a permeation of ondansetron across shed snake skin as a model membrane", Journal of Pharmacy and Pharmacology, Jun. 1, 2001, pp. 789-794, vol. 53, No. 6, Royal Pharmaceutical Society of Great Britain, GB.
Krishnaiah, Y.S.R., et al., "Penetration-Enhancing Effect of Ethanolic Solution of Menthol on Transdermal Permeation of Ondansetron Hydrochloride Across Rat Epidermis", Drug Delivery, Jan. 1, 2008, pp. 227-234, vol. 15, No. 4, Academic Press, Orlando, FL, US.

* cited by examiner

*Primary Examiner* — San-Ming Hui
(74) *Attorney, Agent, or Firm* — Sughrue Mion, PLLC

(57) ABSTRACT

A formulation for oral transmucosal administration of at least one active principle with antispasmodic and/or analgesic effect, including the active principle in base form and/or in salt form, an aqueous alcohol solution titrating at least 35° alcohol by weight, the active principle being present in a state of stable and complete dissolution in the aqueous alcohol solution. Also, a method of preparing this formulation and its use for treating spastic crises.

9 Claims, No Drawings

FORMULATION FOR ORAL TRANSMUCOSAL ADMINISTRATION OF ANALGESIC AND/OR ANTISPASMODIC MOLECULES

CROSS REFERENCE TO RELATED APPLICATIONS

This application is a National Stage of International Application No. PCT/FR2010/050039, filed Jan. 12, 2010, which claims priority from French Patent Application No. 0950145, filed Jan. 13, 2009, the contents of all of which are incorporated herein by reference in their entirety.

The present invention relates to a formulation for instantaneous systemic oral transmucosal administration of at least one active principle having an analgesic and/or antispasmodic action.

The invention also relates to a method of preparing and using this formulation for treating and preventing spastic and painful crises.

Some organic pathologies linked to inflammatory processes are manifested in violent, unpredictable, and painful spastic crises, often located in the hepato-entero-colic system (spasmodic colitis and cholecystitis) or the urinogenital system (nephritic colic and cystitis). These are reactive spasms of the organs that cause functional impotence states sometimes requiring urgent treatment, since lack of treatment can lead to a syncopal state.

Two molecules are particularly well known among the treatments used to attenuate or eliminate these spasms: phloroglucinol marketed under the name Spasfon® and tiemonium marketed under the name Visceralgine®. These two active principles, which dominate the antispasmodics sector, are quaternary ammonium compounds, lipophilic molecules of low molecular weight.

Phloroglucinol is a spasmolytic musculotropic antispasmodic with particularly marked action on the ureter and the Oddi sphincter. It acts directly on the smooth fibers and behaves as a calcium antagonist at the level of the muscular membrane by raising cyclic 3'5'-AMP by inhibiting the enzyme phosphodiesterase.

Tiemonium methysulfate is an antispasmodic for painful acute digestive (colitis, cholecystitis), gynecological (dysmenorrhea), and urinary (nephritic colic) symptoms. It has a two-fold pharmacological action: a papaverinic musculotropic action, acting directly on the smooth muscle fibers like phloroglucinol, as a calcium antagonist at the level of the cellular membrane, and a moderate parasympatholytic action at the level of the ganglions of the sympathetic system but becoming ganglioplegic only at very high doses.

Apart from these antispasmodics, in the context of treating spastic crises, it is possible also to administer to the suffering patient an analgesic to reduce their pain.

Of the analgesics likely to be administered for spastic crises, nefopam is particularly suitable. It is a pure central, lipophilic or amphiphilic action non-opiate analgesic, used in the treatment of moderate to intense pain, in particular post-operative pain. It may potentially be used for the urgent treatment of so-called "spastic" painful pathologies, such as spasmodic colitis, nephritic colitis or post-operative or post-visceral trauma pain. It has the advantages of not being a respiratory depressant and not inducing any reduction of intestinal transit.

Although these molecules used to treat spastic problems, both antispasmodic molecules and analgesic molecules, are recognized as having a proven activity, their administration to treat a spastic crisis nevertheless encounters numerous difficulties.

Analgesics of the nefopam type are mainly administered in intravenous or intramuscular form.

As for the major antispasmodics, they are generally administered by the oral route in pill or orally disintegrating tablet (ODT) form. They may equally be administered in suppositories or in intravenous or intramuscular injectable form.

The fastest and most effective administration route, regardless of the molecule, is the intravenous or intramuscular route. However, this administration route requires a prescription, the use of specific equipment, and dedicated personnel. It is of high cost and its use is burdensome for the patient, and unsuitable for self-medication.

In the context of treating spastic crises, it is thus preferable to avoid the injectable forms and to administer the antispasmodic or analgesic molecules by the oral route.

The best-known oral route is administration via the enteral route in pill or ODT form, but this administration route is not suitable for antispasmodics or analgesics either.

Firstly, violent spastic crises are often associated with digestive problems. The target patients may be extremely sensitive to taking medication orally and may reject them instantly.

Apart from this difficulty depending on the condition of the patient and their capacity to absorb a pharmaceutical formulation without rejecting it, under the best absorption conditions a delay of at least about 40 minutes (min) must be expected before the beginning of a pharmacodynamic effect leading to a reduction of spasms and pain, which is a delay out of all proportion to the expectations of a suffering patient.

When they are introduced into the digestive tract and the stomach, lipophilic antispasmodic and analgesic molecules suffer what is called the "digestive first pass" effect, i.e. deterioration and losses linked to the stomach environment or to intestinal physiology variations. They are then subjected to what is called the "hepatic first pass" effect that causes them to be metabolized and/or more or less intensely deteriorated, with numerous metabolites being produced, that are, for the most part, inactive or toxic and cause side effects.

The truly bioavailable dose of active principles resorbed by the digestive tract is therefore extremely low.

With nefopam it is virtually nil, because all three of its main metabolites have no pharmacological activity.

As for the antispasmodics, only a residual part actually reaches the smooth muscular membranes and inhibits the enzyme phosphodiesterase: on average at best 40% to 50% with phloroglucinol and 10% to 15% with tiemonium. This is as true for a coated pill as for a ODT form. The ODT form, although indicated for sublingual use, is not able to dissolve perfectly the antispasmodic molecules, which are always amphiphilic or hydrophobic, in the oral environment, said molecules being nevertheless swallowed and metabolized in the digestive tract and the liver.

Thus there are several serious problems.

The first problem is that a substance must be absorbed by a patient who is already weakened and susceptible to reflex vomiting. The medication must not be rejected when swallowed and the active principle must be sufficiently absorbed despite any digestive problems of the patient.

A second difficulty resides in the administration of a sufficient dose of medication to the patient, given the patient's weight and the dilution and dispersion of this active principle in the organism, so that only the meaningfully-active part reaches the hepato-entero-colic or urino-genital systems with antispasmodics, or the central nervous system with analgesics.

Another problematic is the latency time caused by metabolization and diffusion in the organism before the molecule acts and the patient feels the benefits.

Administering antispasmodics and analgesics by the digestive route is therefore inappropriate. The bioavailability and action delay of these molecules are surprisingly at odds with the urgency of the treatment that calls for them.

Treating painful spastic pathologies of the organs is therefore difficult and problematic at present and the available therapeutic means are unsuitable. There remains a need for a dosage formulation that is simple to produce, acts quickly, is readily available and manageable by patients on their own, that is neither a conventional formulation, too slow and random, nor an injectable formulation, usable exclusively by the medical and nursing profession, but rather a formulation adapted to relieve the spasm in the shortest possible time with the most economical dose.

This is the need that is addressed by the present invention in proposing a specific dosage formulation, in very specific solution form, guaranteeing instantaneous oral transmucosal administration of at least one analgesic active principle for treating a spastic crisis, with an effective does equivalent to that of an intravenous or intramuscular dose, comprising:
   at least one active principle present in base form and/or in salt form, chosen from peripheral action antispasmodics and nefopam;
   an aqueous alcohol solution titrating at least 35° alcohol; and
   optionally, another active principle present in base form and/or in salt form, chosen from central action analgesics;
   the active principle(s) being present in a state of stable and complete dissolution in the aqueous alcohol solution.

The invention also proposes a preparation method and the use of this formulation for treating spastic pathologies.

In the context of the present invention, by spastic crisis or spastic pathology is meant any hyperactivity of the smooth muscle fibers of the organs, whatever its physiopathological source, causing chronic painful syndromes justifying therapeutic attention.

Compared to existing formulations, the formulation of the invention is advantageously very simple to produce and to use and allows instantaneous and complete oral transmucosal passage of a therapeutic preparation based on analgesic and/or antispasmodic molecules, limiting any dilution by saliva and swallowing of the molecules, which are delivered virtually instantaneously to the vascular system for distribution of the whole of the dose to the receptors in the organs specific to their pharmacological activity. The dose of active principle administered is furthermore lower than the dose that needs to be introduced in existing oral formulations.

The formulation is simple to use, of relatively low cost, readily available, and relatively non-invasive. It makes it possible to administer an immediately bioavailable quantity of analgesics and/or antispasmodics so as to be able to treat spastic crises very quickly and effectively. It also has the advantage of making it possible to combine in the same formulation both a peripheral action antispasmodic and a central action analgesic.

The formulation of the invention is useful both for urgent treatment in an emergency, to relieve a spasm quickly with just the effective dose, without having to use the intravenous or intramuscular route, and also for self-medication because it makes it possible to supply appropriate doses.

Other features and advantages emerge from the following description of the invention.

Thus a first aspect of the invention provides a formulation for oral transmucosal administration of at least one active principle for treating a spastic crisis, comprising:
   at least one active principle present in base form and/or in salt form, chosen from peripheral action antispasmodics and nefopam;
   an aqueous alcohol solution titrating at least 35° alcohol; and
   optionally, another active principle present in base form and/or in salt form, chosen from central action analgesics.

The formulation very preferably consists of only these elements.

The active principle(s) is/are present in a stable and completely dissolved state in the aqueous alcohol solution, with a volume that is preferably less than 2 millimeters (mL), so as to allow rapid absorption of said active principle via the mucosa of the oral cavity.

Thus the invention provides a formulation including an aqueous alcohol solution containing:
   an antispasmodic with peripheral action only;
   an antispasmodic with peripheral action associated with a central action analgesic, such as paracetamol or nefopam;
   nefopam only; or
   nefopam combined with another central action analgesic, such as paracetamol.

The pharmaco-therapeutic category to which a molecule belongs is that assigned to it in its Marketing Authorization (or Notice of Compliance).

In particular, phloroglucinol and tiemonium are listed in the VIDAL Dictionary under "antispasmodics" and nefopam and paracetamol under "non-opiate analgesics".

The expression "transmucosal route" refers to any passive passage of a lipophilic or amphiphilic molecule presented in a stable dissolved state through the mucosa of the tongue under the tongue, of the gums, of the palate, of the cheek, or any other mucosa of the oral cavity.

The expression "stable and completely dissolved state" refers to a solution state rendering the active principle in the molecular and weakly ionized state in its solution medium, this solution state preventing any possibility of inopportune recrystallization. This stable and completely dissolved state may be monitored immediately on use of the formulation of the invention by evaluating the visual appearance of the solution obtained (measurement of the degree of limpidity), then at the level of the filtration residues (appearance or non-appearance of crystals), and finally in the medium-term and long-term during stability tracking tests at varying temperatures and relative humidities.

The expression "aqueous alcohol solution titrating X degrees alcohol" refers to a solution presenting a degree of alcohol equal to X, corresponding to the ratio between the volume of pure (100°) alcohol contained in the aqueous alcohol solution and the total volume of that solution. The degree of alcohol of the aqueous alcohol solution varies as a function of the degree of the alcohol used to form the solution and the water/alcohol ratio of the solution. For example, for 100° alcohol and a water/alcohol ratio of 50/50, the aqueous alcohol solution titrates 50° alcohol.

The analgesic and/or antispasmodic active principle is present in base form and/or in salt form, for example in succinate, hydrochloric, sulfate, or methysulfate form.

The analgesic active principle is chosen from all central action non-opiate analgesics, and there may be mentioned by way of non-limiting example lipophilic or amphiphilic active principles such as nefopam or paracetamol.

The active principle intended for treatment of spasmodic crises is preferably chosen from all antispasmodics, such as phloroglucinol or tiemonium.

The formulation preferably includes nefopam, paracetamol, phloroglucinol, or tiemonium.

In one particular embodiment of the invention, the formulation includes at least two different active principles: a central action analgesic and an exclusively peripheral (i.e. visceral) action antispasmodic.

The analgesic is chosen from nefopam and paracetamol.

The antispasmodic is chosen from phloroglucinol and tiemonium.

This combination covers simultaneously and in a single low-dose administration the usually separate registers of treating both pain and spasm.

This treatment is for single administration for two-fold instant therapeutic action.

A particularly appropriate example consists in combining in the formulation nefopam and phloroglucinol.

The formulation of the invention may equally include a pH corrector agent. By pH corrector agent is meant any acid agent or any basic agent not degrading the physico-chemical characteristics of the active principle or principles.

The pH corrector agent is preferably chosen from carbonates and bicarbonates of sodium, monosodium or disodium phosphates, triethanolamine, sodium hydroxide (NaOH), and potassium hydroxide (KOH), and also hydrochloric, sulfuric, phosphoric, citric, malic, lactic, succinic, and/or butyric acid agents.

The formulation of the invention preferably takes the form of an aqueous alcohol solution containing 30% to 95% alcohol and 5% to 70% water by volume. The formulation of the invention even more preferably takes the form of an aqueous alcohol solution containing 40% to 85% alcohol and 60% to 15% water by volume. This corresponds to proportions in terms of mass that are very similar, given the density of water (approximately 1 gram per cubic centimeter ($g/cm^3$)) and that of ethanol (0.79 $g/cm^3$).

The aqueous alcohol solution has a degree of alcohol of at least 35°, preferably 35° to 70°, even more preferably 35° to 60°, and ideally around 40° to 50°. This degree of alcohol is particularly suitable for analgesic and/or antispasmodic molecules and allows their constantly stable and complete dissolution as well as their quasi-instantaneous total absorption via the oral mucosa.

The aqueous alcohol solution is advantageously the only solvent used in the formulation of the invention.

Furthermore, the alcohol in the aqueous alcohol solution serves not only as a diluent for molecules that are not soluble in water but also to promote faster transmucosal absorption, at a rate that increases as a function of the degree of alcohol used. The degree of alcohol of the formulation must nevertheless not exceed 70° because a higher degree would be incompatible with a pharmaceutical substance for oral application because it could burn the mucosa.

In a preferred and especially suitable embodiment of the invention, the aqueous alcohol solution is based on water and ethanol.

By way of illustration, the dissolution coefficient of phloroglucinol in ethanol makes it possible to obtain complete dissolution of said active principle at the rate of 20 milligrams (mg) of phloroglucinol in 0.75 mL of approximately 40° ethanol.

Similarly, the coefficient of dissolution of tiemonium methylsulfate in ethanol makes it possible to obtain complete dissolution of said active principle at the rate of 10 mg of tiemonium in 0.75 mL of approximately 40° ethanol. The coefficient of dissolution of nefopam in ethanol makes it possible to obtain complete dissolution of said active principle at the rate of 20 mg of nefopam in 1 mL of approximately 40° ethanol.

The coefficient may be modulated as a function of the degree of alcohol required for accelerated transmucosal passage and the preferred water/ethanol dissolution ratio employed.

The pH of the formulation of the invention is preferably in the range 5.0 to 9.0, more preferably in the range 5.5 to 7.5. These pH values are favorable for optimum absorption of the solution.

The formulation of the invention enables the active principle to cross the oral mucosa passively within 6 seconds (s) to 10 s from administration. This very fast absorption makes it possible to prevent stagnation of the solution and the active principle in the oral atmosphere and their inopportune mixing with saliva, which is liable to degrade them, which would introduce a discontinuity into the continuity and stability of dissolution of the active principle or principles. This short time also makes it possible to prevent reflex swallowing of the solution and the active principle that it contains.

The oral transmucosal passage of the active principle present in the dissolution state of the invention on the side of the external epithelial membrane, consisting of phospholipidic structures that absorb passively by elective affinity the lipophilic molecules presented in a stable and completely dissolved state, is based on osmotic or pulling pressure towards the other side of said membrane, in which jointly participate the concentration of dissolved active principle and that of the aqueous alcohol solution concerned. The activity and strength of the osmotic pressure increase with the degree of alcohol that serves as absorption promoter. A degree of alcohol suitable for phloroglucinol, tiemonium or nefopam is 35° to 60°, preferably approximately 40° to 50°. This makes it possible simultaneously to obtain and adjust the best coefficient of dissolution and stabilization of the molecule and promotion of its transmucosal passage within 4 s to 10 s, for a volume less than or equal to 1 mL.

A particularly suitable example uses 0.75 mL of aqueous alcohol solution with a degree of alcohol of approximately 40° for 10 mg of tiemonium methylsulfate, 20 mg of phloroglucinol, or 10 mg of nefopam.

Another particularly suitable example uses 1 mL of aqueous alcohol solution with a degree of alcohol of approximately 40° for 25 mg of tiemonium methylsulfate, 40 mg of phloroglucinol, or 20 mg of nefopam.

The mucosa of the mouth have a very dense quasi-spongy array of micro-vessels, with the result that molecules, either of the alcohol solvent or of the dissolved active principle, that pass through the lipophilic pores of the epithelial membrane are instantly captured by the micro-circulation of blood and collected toward the sublingual veins, and then the jugular veins going to the heart. This phenomenon is accentuated by the presence of the alcohol, which causes vasodilation and increases the local micro-vascular flow rate of the mucosa.

Because of this raised circulatory flow rate, there is therefore never equilibrium on respective opposite sides of the epithelial membrane: the concentration in the mouth always remains higher, until exhaustion of the mechanism for lack of molecules to absorb.

Thus, in distinct contrast to all other so-called "sublingual" forms, all of the alcohol and the active principle of the invention dissolved therein passes through the mucosa.

Using the dosage formulation of the invention makes it possible to administer passively a dose of analgesics and/or antispasmodics absorbed immediately when deposited on the mucosa, to be instantly distributed via the vascular route, with no delay preceding its pharmacological action, and without suffering the preliminary destructive effects of digestive and hepatic passage. The dosage formulation of the invention therefore makes possible immediate and complete tissue absorption of the analgesic and/or antispasmodic molecules, followed by their distribution in the central circulation of the organism, generating a fast "flash" type pharmacological response.

For example, with a dosage formulation of the invention prepared from 40 mg of phloroglucinol dissolved in 1 mL of a 40° ethanol solution, it is possible to administer a very significant dose of phloroglucinol quasi-instantaneously and passively. This 40 mg dose is higher than the theoretically available maximum fraction of a dose normally administered via the oral route (62.25 mg), which is 40% to 50% (31.12 mg) at best of the dose usually administered via the oral route.

Likewise with a dosage formulation of the invention prepared from 10 mg of tiemonium dissolved in 0.75 mL of a 40° ethanol solution, it is possible to administer quasi-instantaneously and passively a dose higher than the theoretically-available maximum fraction of a dose normally administered via the oral route (50 mg), which is 10% to 15% (approximately 5 mg) at best of the dose usually administered via the oral route.

In another example, with a dosage formulation of the invention produced from 20 mg of nefopam dissolved in 1 mL of a 40° ethanol solution, it is possible to administer quasi-instantaneously and passively a dose identical to the fraction normally administered by intravenous injection (20 mg of nefopam hydrochloride per 2 mL of solution).

With the formulation of the invention, the bioavailability of the dose administered by the local transmucosal route is complete.

The aqueous alcohol solution of the invention, titrating at least 35° alcohol, also has the advantage of dissolving the analgesic and antispasmodic molecules, even though they are lipophilic, which allows their spontaneous transmucosal absorption and protects the pharmaceutical formulation against microbiological contamination without it being necessary to introduce antibiotic preservatives.

Thus the aqueous alcohol solution of the invention has a four-fold efficacy:
- it serves as a solvent for the analgesic and/or antispasmodic active principle for treating a spastic crisis, which are lipophilic or amphiphilic molecules of low molecular weight;
- it activates transmucosal passage of this dissolved active principle presented in the molecular state in this way at the level of the lipophilic membrane;
- the degree of alcohol increases the rate of transmucosal absorption in two ways, by osmotic effect and by causing reflex micro-vascular vasodilation, which accelerates the local micro-circulatory flow; and
- it is its own stability agent, which avoids the use of the usual additives.

The present invention advantageously offers very simple production and very good dosage stability: the extremely simplified water/alcohol solution guarantees dissolution of the active principle and makes it possible to dispense with most of the excipients usually employed for conventional pharmaceutical preparations, including preservatives.

Thus it makes it possible to reduce production costs and at the same time to reduce the risks of intolerance and possible interaction between active principle and excipients.

Another advantage is that there is a very short delay in the pharmacodynamic action of the dosage form of the invention compared to the slow absorption of existing antispasmodic-based medications that have a delay of at least 40 min between taking the medication and the beginning of their analgesic or antispasmodic pharmacological action.

The quasi-instantaneous pharmacological delivery may enable a patient to administer a substance with an effect equivalent to the efficacy of a flash intravenous injection, without the drawbacks linked to this type of administration. It also enables urgent treatment in hospitals without the need to prepare, fit, and monitor a venous catheter and thus without risk of nosocomial contamination.

This administration route is much better in terms of simplicity and of non-traumatic administration availability, but also of unit and therapeutic cost compared to the administration routes for existing molecules intended to treat spastic crises. The gain in terms of dose/effect ratio is at least 40% to 50%. With the formulation of the invention, an at least 40% to 50% lower dose is employed to obtain a therapeutic effect without delay. The analgesic and/or antispasmodic molecules administered encounter no significant obstacle to their instantaneous distribution via the arteries to the target receptors of the smooth fibers or the central nervous system, which they reach in a few seconds, and the basic dose administered is low, comparable to the bioavailable dose needed for exercising the required pharmacological activity. The dose of active principle contained in the formulation of the invention is thus lower than the doses conventionally administered. This dose depends of course on the required effect. It is preferably in the range 2 mg to 50 mg of active principle in volumes of aqueous alcohol solution in the range 0.5 mL to 2 mL.

Moreover, the oral mucosa having an extremely large total absorption area, made greater by its creased villous tissue character, administration of the formulation of the invention is free of any risk of untimely swallowing or misrouting. It enables extremely fast transmucosal passage, which prevents dissolution in the saliva and swallowing of the administered active principle, with the advantage of not destabilizing the mucosa with various elements or excipients. Moreover, the formulation of the invention is particularly suitable for patients suffering violent spastic crises accompanied by nausea syndromes because it avoids any possibility of rejection of the administered medication by vomiting.

Moreover, the effects of the alcohol are insignificant. For example, 0.75 mL of a 40° ethanol aqueous alcohol solution could only result in a alcohol blood level below 0.004 grams per liter of blood, according to the official Widmark reference formula, i.e. $1/12$ of the legal limit in France, which is set at 0.5 grams per liter of blood. Moreover, the initial pulmonary expulsion of the alcohol solution allows virtually complete elimination of the ethanol in the form of vapor extracted via the respiratory route and exhaled before the ethanol can be distributed in the organism. The alcohol vector is thus eliminated almost completely via the respiratory parenchyma.

A second aspect of the invention provides a method of preparing the formulation.

A particularly suitable method of producing the dosage formulation of the invention comprises the following steps:

mixing alcohol and purified water and introducing into this mixture at least one analgesic and/or antispasmodic active principle;

stirring the preparation until a homogeneous suspension is obtained;

further stirring to complete dissolution of the active principle; and filtering.

In a preferred implementation of the invention the method comprises the following steps:

mixing ethanol and purified water and introducing into this mixture nefopam or phloroglucinol or tiemonium methylsulfate;

stirring the preparation, preferably for 10 min to 60 min, until a homogeneous suspension and complete dissolution of the active principle are obtained; and filtering.

The method may comprise the following steps before filtration:

progressively introducing a pH corrector agent until a required pH from 5.0 to 8.0 is obtained;

further stirring, preferably for 5 min to 30 min to complete dissolution of the active principle; and adding water if necessary to make up to the required volume.

The present invention may be used for instantaneous systemic administration at low useful analgesic doses, notably of non-opiate analgesics such as nefopam, or antispasmodics, notably pholoroglucinol or tiemonium.

The formulation of the present invention may in particular be used to produce a medication for treating spastic crises, in particular violent crises such as spasmodic colitis, nephritic colic, cholecystitis or post-operative or post-trauma pelvic, gynecological, or gyneco-obstetric visceral pain by oral transmucosal administration.

Such a medication for oral transmucosal administration has therapeutic activity that relieves the spasm and/or calms the pain in a very short time and at low doses compared to conventional doses. A preferred medication comprises the formulation of the invention combining an antispasmodic molecule with a central non-opiate analgesic molecule such as nefopam or paracetamol.

The formulation of the invention, corresponding to a very small volume of liquid, is very easy to administer. A patient may easily place it in their mouth in direct contact with a precise but smaller area of the mucosa of the mouth, of the gums or under the tongue.

The patient should preferably place the formulation of the invention in a mucosal area sheltered from salivary secretions, for example the gutter of the cheek, defined between the lower external ring of the gums and the mucosal wall of the lower internal faces of the cheeks and lower lip. This channel represents on average a closed reservoir that is approximately 18 centimeters (cm) long and in the range 1 cm to 1.5 cm deep, i.e. a mucosal absorption area of 35 square centimeters ($cm^2$) to 55 $cm^2$.

According to a final aspect of the invention, the formulation requires specific industrial packaging in order to allow its safe, simple, and ergonomic use and to prevent the active principle from being degraded by contact with air.

One particular example uses opaque glass or flexible metal-plastic or plastic packaging, preferably of small size, filled in an inert atmosphere such as nitrogen, to protect the stability of the composition and the impermeability to oxygen and to radiation. These forms of packaging guarantee dissolution and stability over time of the dissolved active principles in aqueous alcohol solution of the invention.

These forms of packaging preferably include a cannula allowing precise deposition of the solution of the invention in contact with an appropriate area of the mucosa.

For comfortable use by the patient and for easy transportation, dedicated sealed packages may preferably be used for packaging. Even more preferably, the dosage formulation of the invention is packaged in single-dose packages of 0.5 mL to 2 mL, able to provide an adequate dose of active principle.

This packaging is advantageously easy to transport and allows easy use of the dosage formulation at any time of day.

Examples of formulations of the invention may be mentioned that are particularly suitable for producing antispasmodic/analgesic efficacy:

FORMULATION 1

25 mg Tiemonium Methylsulfate, 1.00 mL of Approximately 40° Ethanol tiemonium methylsulfate (active principle): 25.0 mg
95° ethanol (diluent and absorption promoter): 0.40 mL
purified water (diluent): qsp 1.00 mL This first formulation example may be produced using the method described below for a batch of 1000 doses, i.e. 1 liter (L).

Into a stainless steel tank introduce 0.40 L of 95% V/V ethanol and 0.6 L of purified water.

Introduce into the aqueous alcohol solution 25 g of tiemonium methylsulfate.

Using a helical stirrer, stir the preparation for 20 min to 40 min until a homogeneous suspension is obtained.

Further stirring to complete dissolution of the tiemonium.

Filter the preparation using a 5 μm (μm) polypropylene or like filter and dispense the preparation into 1.00 mL single-dose bottles.

FORMULATION 2

10 mg Tiemonium Methylsulfate, 0.75 mL of Approximately 40° Ethanol tiemonium methylsulfate (active principle): 10.0 mg
95° ethanol (diluent and absorption promoter): 0.30 mL
purified water (diluent): qsp 0.75 mL This second formulation example may be produced using the method described below for a batch of 1000 doses, i.e. 0.75 L.

Into a stainless steel tank introduce 0.30 L of 95% V/V ethanol and 0.45 L of purified water.

Introduce into the aqueous alcohol solution 10 g of tiemonium methylsulfate.

Using a helical stirrer, stir the preparation for 20 min to 40 min until a homogeneous suspension is obtained.

Further stirring to complete dissolution of the tiemonium.

Filter the preparation using a 5 μm polypropylene or like filter and dispense the preparation into 0.75 mL single-dose bottles.

FORMULATION 3

20 mg Phloroglucinol, 0.75 mL of Approximately 40° Ethanol phloroglucinol (active principle): 20.0 mg
95° ethanol (diluent and absorption promoter): 0.30 mL
purified water (diluent): qsp 0.75 mL This second formulation example may be produced using the method described below for a batch of 1000 doses, i.e. 0.75 L.

Into a stainless steel tank introduce 0.30 L of 95% V/V ethanol and 0.45 L of purified water.

Introduce into the aqueous alcohol solution 20 g of phloroglucinol.

Using a helical stirrer, stir the preparation for 20 min to 40 min until a homogeneous suspension and complete dissolution of the phloroglucinol is obtained.

Filter the preparation using a 5 μm polypropylene or like filter and dispense the preparation into 0.75 mL single-dose bottles.

FORMULATION 4

40 mg Phloroglucinol, 1.00 mL of Approximately 40° Ethanol phloroglucinol (active principle): 40.0 mg
95° ethanol (diluent and absorption promoter): 0.40 mL
purified water (diluent): qsp 1.00 mL This formulation example may be produced using the method described below for a batch of 1000 doses, i.e. 1.00 L.

Into a stainless steel tank introduce 0.40 L of 95% V/V ethanol and 0.60 L of purified water.

Introduce into the aqueous alcohol solution 40 g of phloroglucinol.

Using a helical stirrer, stir the preparation for 20 min to 40 min until a homogeneous suspension is obtained.

Further stirring to complete dissolution.

Filter the preparation using a 5 μm polypropylene or like filter and dispense the preparation into 1.00 mL single-dose bottles.

FORMULATION 5

20 mg Nefopam, 1.0 mL of 40° Ethanol nefopam (active principle): 20.0 mg
95° ethanol (diluent and absorption promoter): 0.40 mL
purified water (diluent): qsp 1.00 mL This formulation example may be produced using the method described below for a batch of 1000 doses, i.e. 1.00 L.

Into a stainless steel tank introduce 0.40 L of 95% V/V ethanol and 0.60 L of purified water.

Introduce into the aqueous alcohol solution 20 g of nefopam.

Using a helical stirrer, stir the preparation for 20 min to 40 min until a homogeneous suspension is obtained.

Further stirring to complete dissolution.

Filter the preparation using a 5 μm polypropylene or like filter and dispense the preparation into 1.00 mL single-dose bottles.

FORMULATION 6

10 mg Nefopam, 0.75 mL of 40° Ethanol nefopam (active principle): 10.0 mg
95° ethanol (diluent and absorption promoter): 0.30 mL
purified water (diluent): qsp 0.75 mL This formulation example may be produced using the method described below for a batch of 1000 doses, i.e. 0.75 L.

Into a stainless steel tank introduce 0.30 L of 95% V/V ethanol and 0.45 L of purified water.

Introduce into the aqueous alcohol solution 10 g of nefopam.

Using a helical stirrer, stir the preparation for 20 min to 40 min until a homogeneous suspension and complete dissolution of the phloroglucinol are obtained.

Filter the preparation using a 5 μm polypropylene or like filter and dispense the preparation into 0.75 mL single-dose bottles.

FORMULATION 7

10 mg Nefopam, 20 mg Phloroglucinol, 1.0 mL of 40° Ethanol nefopam (active principle): 10.0 mg
phloroglucinol (active principle): 20.0 mg
95° ethanol (diluent and absorption promoter): 0.40 mL
purified water (diluent): qsp 1.00 mL This formulation example may be produced using the method described below for a batch of 1000 doses, i.e. 1.0 L.

Into a stainless steel tank introduce 0.40 L of 95% V/V ethanol and 0.60 L of purified water.

Introduce into the aqueous alcohol solution 10 g of nefopam and 20 g of phloroglucinol.

Using a helical stirrer, stir the preparation for 20 min to 40 min until a homogeneous suspension and complete dissolution of the phloroglucinol and the nefopam is obtained.

Filter the preparation using a 5 μm polypropylene or like filter and dispense the preparation into 1.00 mL single-dose bottles.

FORMULATION 8

10 mg Tiemonium, 125 mg Paracetamol, 1.0 mL of 45° Alcohol tiemonium methylsulfate (active principle): 10.0 mg
paracetamol (active principle): 125.0 mg
95° ethanol (diluent and absorption promoter): 0.45 mL
purified water (diluent): qsp 1.00 mL This formulation example may be produced using the method described below for a batch of 1000 doses, i.e. 1.00 L.

Into a stainless steel tank introduce 0.45 L of 95% V/V ethanol and 0.55 L of purified water.

Introduce into the aqueous alcohol solution 10 g of tiemonium methylsulfate and 125 g of paracetamol.

Using a helical stirrer, stir the preparation for 20 min to 40 min until a homogeneous suspension is obtained.

Filter the preparation using a 5 μm polypropylene or like filter and dispense the preparation into 1.00 mL single-dose bottles.

FORMULATION 9

40 mg Phloroglucinol, 125 mg Paracetamol, 1.0 mL of 45° Alcohol phloroglucinol (active principle): 40.0 mg
paracetamol (active principle): 125.0 mg
95° ethanol (diluent and absorption promoter): 0.45 mL
purified water (diluent): qsp 1.00 mL This formulation example may be produced using the method described below for a batch of 1000 doses, i.e. 1.00 L.

Into a stainless steel tank introduce 0.45 L of 95% V/V ethanol and 0.55 L of purified water.

Introduce into the aqueous alcohol solution 40 g of phloroglucinol and 125 g of paracetamol.

Using a helical stirrer, stir the preparation for 20 min to 40 min until a homogeneous suspension is obtained.

Filter the preparation using a 5 μm polypropylene or like filter and dispense the preparation into 1.00 mL single-dose bottles.

Of course, the invention is obviously not limited to the examples described above, and to the contrary covers all variants thereof.

The invention claimed is:

1. A formulation for oral transmucosal administration of one or more active principles for treating a spastic crisis,
   wherein said one or more active principles are selected from the group consisting of tiemonium, phloroglucinol, and nefopam, with said one or more active principles being the only active principles in said formulation,
   wherein said one or more active principles are present in base form and/or in salt form,
   wherein when said tiemonium is present in said formulation, it is present in an amount between 2-25 mg; wherein when said phloroglucinol is present in said formulation, it is present in an amount between 2-40 mg; and wherein when said nefopam is present in said formulation, it is present in an amount between 2-20 mg, provided that the total amount of active principle in said formulation is between 2-50 mg,
   and wherein in said formulation, said one or more active principles are present in a state of stable and complete dissolution in an aqueous ethanol solution, said aqueous ethanol solution titrating to at least 35° ethanol and comprising 40% to 85% ethanol and 15% to 60% water.

2. The formulation according to claim 1, wherein the aqueous ethanol solution titrates to 35° to 70° ethanol.

3. The formulation according to claim 1, wherein the formulation further comprises a pH corrector agent.

4. The formulation according to claim 3, wherein the pH corrector agent is selected from the group consisting of: carbonates and bicarbonates of sodium; monosodium or disodium phosphates; triethanolamine; sodium hydroxide; potassium hydroxide; hydrochloric acid; sulfuric acid; succinic acid; butyric acid; phosphoric acid; citric acid; malic acid; and lactic acid.

5. The formulation according to claim 1, wherein said formulation has a pH from 5.0 to 9.0.

6. A method for preparing the formulation according to claim 1, wherein said method comprises the following steps:
   mixing ethanol and purified water and introducing into this mixture at least one active principle selected from the group consisting of tiemonium, phloroglucinol, and nefopam;
   stirring the preparation until a homogeneous suspension is obtained;
   further stirring to complete dissolution of the active principle; and
   filtering.

7. A method for treating painful spastic crises, comprising administering, through the oral transmucosal route, an effective amount of the formulation of claim 1 to a patient in need thereof.

8. A method for treating spasmodic colitis, nephritic colitis, or post-operative or post-trauma, pelvic, gynecological, or gyneco-obstetric visceral pain, comprising administering, through the oral transmucosal route, an effective amount of the formulation of claim 1 to a patient in need thereof.

9. The formulation of claim 1, wherein the volume of the aqueous ethanol solution is between 0.5-2 ml.

* * * * *